United States Patent
Gerstel et al.

(10) Patent No.: US 8,187,539 B2
(45) Date of Patent: May 29, 2012

(54) DEVICE AND METHOD FOR DETERMINING MATERIAL PROPERTIES BY MEANS OF HPLC

(75) Inventors: Joachim Gerstel, Mülheim an der Ruhr (DE); Jörg Radtke, Neukirchen-Vluyn (DE)

(73) Assignee: Joint Analytical Systems GmbH, Moers (DE)

( * ) Notice: Subject to any disclaimer, the term of this patent is extended or adjusted under 35 U.S.C. 154(b) by 1191 days.

(21) Appl. No.: 11/667,992

(22) PCT Filed: Nov. 11, 2005

(86) PCT No.: PCT/EP2005/055902
§ 371 (c)(1), (2), (4) Date: Oct. 25, 2007

(87) PCT Pub. No.: WO2006/053855
PCT Pub. Date: May 26, 2006

(65) Prior Publication Data
US 2008/0089809 A1    Apr. 17, 2008

(30) Foreign Application Priority Data
Nov. 16, 2004   (DE) .......................... 10 2004 000 042

(51) Int. Cl.
*G01N 30/02* (2006.01)
*B01L 3/00* (2006.01)
(52) U.S. Cl. ............................ 422/70; 422/501; 422/502
(58) Field of Classification Search ................... 422/70, 422/103
See application file for complete search history.

(56) References Cited

U.S. PATENT DOCUMENTS

| | | | |
|---|---|---|---|
| 4,391,778 A * | 7/1983 | Andresen et al. ............... | 422/89 |
| 4,861,989 A | 8/1989 | Vestal et al. | |
| 4,982,097 A * | 1/1991 | Slivon et al. ................... | 250/288 |
| 5,422,007 A | 6/1995 | Nicoud et al. | |
| 6,936,787 B2 * | 8/2005 | Tao et al. ................... | 219/121.51 |
| 7,572,999 B2 * | 8/2009 | Tao et al. ................... | 219/121.52 |

FOREIGN PATENT DOCUMENTS

| | | |
|---|---|---|
| DE | 693 23 382 T2 | 6/1999 |
| JP | 63008540 | 1/1988 |
| JP | 02259558 | 10/1990 |
| JP | 4218763 | 2/1991 |
| JP | 2004257786 | 9/2004 |
| JP | 4351957 | 7/2009 |
| WO | WO03/029809 A1 | 4/2003 |

OTHER PUBLICATIONS

Clark, Jody. "Using High Temperature HPLC for Improved Analysis;" May 1, 2004, p. 1-5; <http://pharmtech.findpharma.com/>.*

(Continued)

*Primary Examiner* — Sam P Siefke
*Assistant Examiner* — Bryan Kilpatrick
(74) *Attorney, Agent, or Firm* — Thorpe North & Western LLP

(57) ABSTRACT

An assembly for determining material properties and/or material concentrations of components of a sample, containing: a chromatographic separating column with a liquid mobile solvent; means for controlling the temperature inside the separating column between room temperature and 250° C.; means for creating a pressure level which is greater than ambient pressure inside the separating column; and a detector with a sample volume adapted to insert the components of the sample, is characterized in that the mobile solvent contains water to a large extent; means are provided for expanding the mobile solvent from the increased pressure level inside the separating column to the ambient pressure and for producing a phase change of the mobile solvent from the liquid to gaseous state; and means are provided for transferring the gaseous mobile solvent containing the components of the sample into the sample volume of the detector.

19 Claims, 3 Drawing Sheets

OTHER PUBLICATIONS

Trones, Roger et al. "Packed capillary high-temperature liquid chromatograph coupled to inductively coupled plasma mass spectrometry;" Journal of Chromatography A, 835, 1999, p. 105-112.*

Sigma-Aldrich online articles/advertisements for "Water" and "Acetonitrile," 2010.*

Zhu, Cuiru et al. "Elevated Temperature HPLC: Principles and Applications to Small Molecules and Biomolecules," LCGC Asia Pacific, vol. 8, No. 1, Mar. 2005, p. 48-59.*

R. Crumping et al., HPLC/ICP-OES determination of water-soluble silicone (PDMS) degradation products in leachates, Fresunius J. Anal Chem, 1999, 347-352, 363.

* cited by examiner

DEVICE AND METHOD FOR DETERMINING MATERIAL PROPERTIES BY MEANS OF HPLC

STATE OF THE ART

The invention relates to an assembly for determining material properties and/or material concentrations of components of a sample, containing:
(a) a chromatographic separating column with a liquid mobile solvent;
(b) means for controlling the temperature inside the separating column between room temperature and 250° C.;
(c) means for creating a pressure level which is greater than the ambient pressure inside the separating column; and
(d) a detector with a sample volume adapted to introduce the components of the sample.

In liquid chromatography, a sample, for example a material mixture of different components, is conducted together with a mobile solvent through a chromatographic separating column. The separating column is filled with a stationary phase. Depending on the polarity of the mobile solvent, on its interaction with the sample, and on the stationary phase, the components reach the outlet of the column after different retention times. A detector is provided to detect the fractions. In such a way, the material mixture is separated and a chromatogram is produced providing information about the presence of a material and, if necessary, its amount. Depending on the mobile solvent, gas chromatography is distinguished from liquid chromatography.

Gas chromatography assemblies which operate with an atomic emission detector (Atomic Emission Detector) are known as GC-AED. A sample is conducted with a gaseous carrier gas through a chromatography column and is afterwards atomized in a microwave plasma. The atoms are thermally excited at temperatures from 2000 to 3000 Kelvin. From the excited state the atoms return to the normal state emitting light at element-specific wavelengths. The radiation is dispersed in a suitable spectrometer and recorded by a detector, for example a diode array. The intensity at the detector is a measure for the amount of an element in the sample. Due to the chromatographic separation the signals appear time-resolved on the detector. A microwave-induced helium plasma is used for the generation of the plasma.

The microwave plasma is generated in a geometrically relatively small plasma torch as it is used for gas chromatography. Advantageously, helium is used as the carrier gas as well as for the generation of the plasma. The torch consists of a quartz or ceramic tube having a diameter of 0.8 to 1 mm. Solvents in which the sample has been dissolved can deposit in the form of organic carbon on the surface of the tube. The wall then becomes particularly hot and can be damaged. Therefore, the solvent is suppressed and is not conducted into the plasma. This is complex.

ICP-OES (Inductively Coupled Plasma-Optical Emission Spectroscopy) is a method suitable as detector for chromatography also. An argon plasma of about 8000 Kelvin is generated by an induction coil. The liquid sample is introduced in the form of an aerosol into the plasma and atomized and excited therein. The emission spectra generated in such a way can be spectrometrically analyzed in the same way as with a microwave plasma. The plasma volume in the ICP torch has an inner diameter of about 1-2 cm. The plasma is so hot that a high yield of atoms and molecules in an excited state is achieved. Alternatively, in ICP-MS atoms are examined by mass spectroscopy rather than optically.

In HPLC (High Performance Liquid Chromatography) the separation is not carried out with a gaseous but with a liquid mobile solvent under high pressure. Organic solvents like acetonitrile, tetrahydrofurane with water or the like are generally used as mobile solvents for the Reversed Phase HPLC. Therefore, very large amounts of organic solvent are used which can cause strong interferences. The above techniques are not adapted for the HPLC. Furthermore, the maximum number of baseline-separated peaks per time unit is smaller than in gas chromatography.

The use of an interface (nebulizer) for liquid chromatography is known for (evacuated) mass spectrometers as detectors. An aerosol of the organic mobile solvent with the sample components is generated in the interface. The aerosol is analyzed by mass spectroscopy thereafter. This is difficult and expensive.

OBJECT OF THE INVENTION

It is an object of the invention to create a device of the abovementioned kind which is simple, cheap and where interferences by the mobile solvent are reduced with a higher sample throughput

DESCRIPTION OF THE INVENTION

According to the invention, this object is achieved in that the mobile solvent contains mainly water, means are provided for expanding the mobile solvent from the elevated pressure level inside the separating column to ambient pressure and for creating of a phase change of the mobile solvent from the gaseous to liquid state, and means are provided for transferring the gaseous mobile solvent containing the components of the sample into the sample volume of the detector.

Contrary to known assemblies, where water is used as mobile solvent the sample containing mobile solvent is introduced without cooling down and in liquid form into the sample volume. Water is expanded at high temperatures to atmospheric pressure. The water evaporates to gas due to the pressure drop. Therefore, the sample is not sprayed in the form of an aerosol into the sample volume, but in gaseous form. The hot gas is then introduced into the sample volume. A difficult cooling is avoided. It is particularly advantageous that only water is present in the matrix and that the assembly, therefore, operates without interfering matrix background. In this way very good detection limits and a high accuracy can be achieved. The components are not contaminated and there are no deposits from a mobile solvent. The portion of hydrogen and oxygen produced by water acts as dopant gas in the sample volume and supports the formation of atoms. Water is a low-cost, environment-friendly raw material which is easily available and which has well known physical and chemical properties.

The separation in the chromatographic column is effected by suitable temperature control. The separation is based on the temperature dependence of the polarity of water which can be controlled over a wide range.

Preferably, the chromatographic separating column is a High Temperature HPLC column. By using high temperature-resistant materials for the column and for the stationary phase the temperature range and thereby the field of application of the assembly can be enlarged.

Preferably, the components of the sample in the sample volume are excited to emit light selectively detectable with respect to the wavelength. The emitted light can be dispersed in an optical spectrometer, for example by means of a grating or a prism, and can be simultaneously recorded time-resolved with a diode array or a CCD detector. Depending on the field of application, spectrographic assemblies simultaneously detecting all wavelengths can be used as well as monochromatic assemblies adjusted to a specific wavelength.

Alternatively, a mass spectrometer for mass spectrometric analysis of the components of the sample in the sample volume is provided. Variations mass-selectively recording or simultaneously recording several masses are suitable mass spectrometers.

In the sample volume a microwave plasma or an inductively coupled plasma can be provided. A microwave plasma which is used for AED assemblies operates at low temperatures in the range of about 2500 K and produces mainly narrow, well-defined atomic lines which are element specific and easy to identify. Background interferences due to molecule residues can occur. On the other hand, an inductively coupled plasma generates ion lines at considerably higher temperatures of about 8000 K and has a considerably higher yield. However, other assemblies for the generation of an emission spectrum can be used also.

In a particularly preferred embodiment of the invention, means are provided for heating the means for transferring the gaseous mobile solvent containing the components of the sample. In particular, these means comprise a heater and optionally control means for controlling the temperature of the gas. By heating the gas, deposits are avoided and a thermal separation of the molecules is achieved. Preferably, the means for heating have a heating power which is sufficient to preferably atomize the components of the sample. Then the gas is just atomized upon entering the sample volume and can be readily detected.

The gas can also be ionized in the interface before its detection.

In one embodiment of the invention one or more additional dopant gases can be fed into the sample volume. Normally, this is not necessary because the mobile solvent delivers sufficient water and oxygen. With the dopant gas the formation of highly volatile materials is supported so that the content of less-volatile compounds can better be measured.

Preferably, a mixture of water and acetonitrile is provided as mobile solvent and the composition of the mixture water: acetonitrile ranges between 95:5 and 55:45 based on the volume.

Furthermore, the assembly is suitable for eluate splitting. The restrictor is supplied with an additional outlet. Only a part of the eluate is transferred into the gaseous state and measured with a suitable detector. A further part is cooled and remains liquid. It is measured in this phase with a conventional detector, for example DAD.

Modifications of the invention are subject matter of the subclaims. Embodiments of the invention are described below in greater detail with reference to the accompanying drawings.
Examples

DESCRIPTION OF THE EMBODIMENTS

Figure 1:
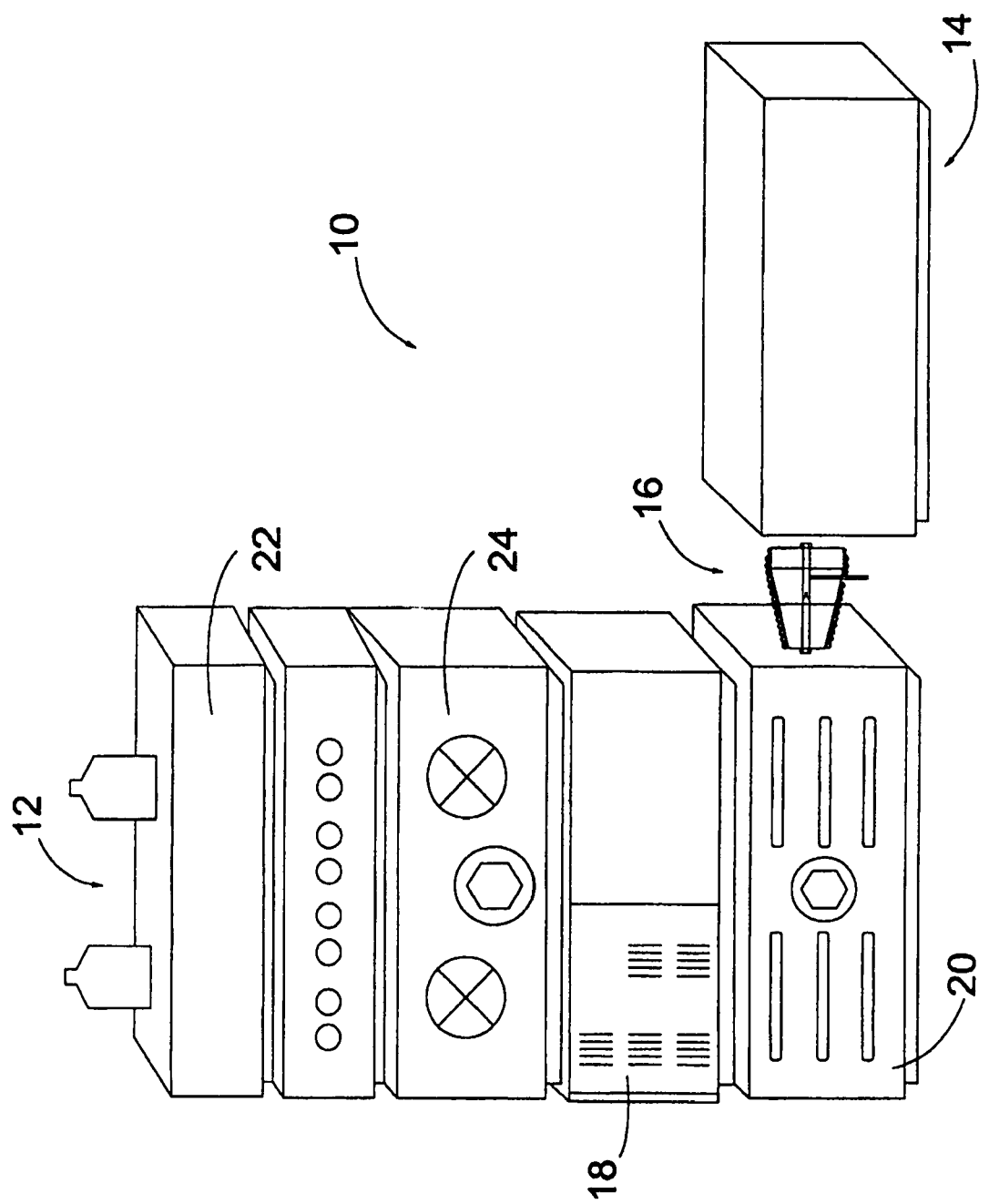
FIG. 1 shows an assembly with a HPLC column, an interface and a detector.

FIG. 1 shows an assembly generally denoted with numeral 10 for determining material properties and/or material concentrations of components of a sample. Samples of natural materials, for example, can be analyzed with such an assembly and steroids or antibiotics can be determined. Every sample comprises a plurality of components which must be separated of each other before the measurement with a detector.

The assembly 10 comprises a sampler and separation device generally denoted with numeral 12, a detector 14 and an interface 16 therebetween.

In the present case the sample is introduced with an autosampler 18 into a conventional HPLC (High Performance Liquid Chromatography) column which is represented in a module 20 with a column furnace. The mobile solvent is degassed in a degasser 22 and pumped with a pump 24 to a pressure of 300 bar.

The HPLC column consists of stainless steel or PEEK material and has an inner diameter in the range of 0.1 to 4.6 mm. The length is 10 to 500 mm. Flow rates in the range of 0.1 µl to 3 ml/min can be generated therewith. The entire material is high temperature-resistant so that the column can be heated to temperatures in the range of 200° C. also without corroding or being damaged otherwise. The stationary phase consists of known temperature-resistant material such as ZirChrom (Registered Trademark) material. It consists of zirconium oxide particles which are coated, for example, with thin layers of elemental carbon. Instead of such a coating, C18 ligands, which are bound to the particles by means of covalent bond, are also suitable. Reversed Phase material, GPC material, and IC material are suitable for the stationary phase also.

The column is heated by the column furnace. A temperature gradient in time is generated thereby between ambient temperature and 200° C. The mobile solvent mainly containing water varies its polarity in wide ranges thereby. In such a way the components contained in the sample are separated while passing the column.

The water portion in the mobile solvent is variable depending on the application. During the analyzing phase the mobile solvent consists of a high percentage of at least 40% of water. After finishing the analyzing phase the portion of organic solvent is increased so that a gradient is formed. In such a way sample residues can be removed from the column.

Figure 2:
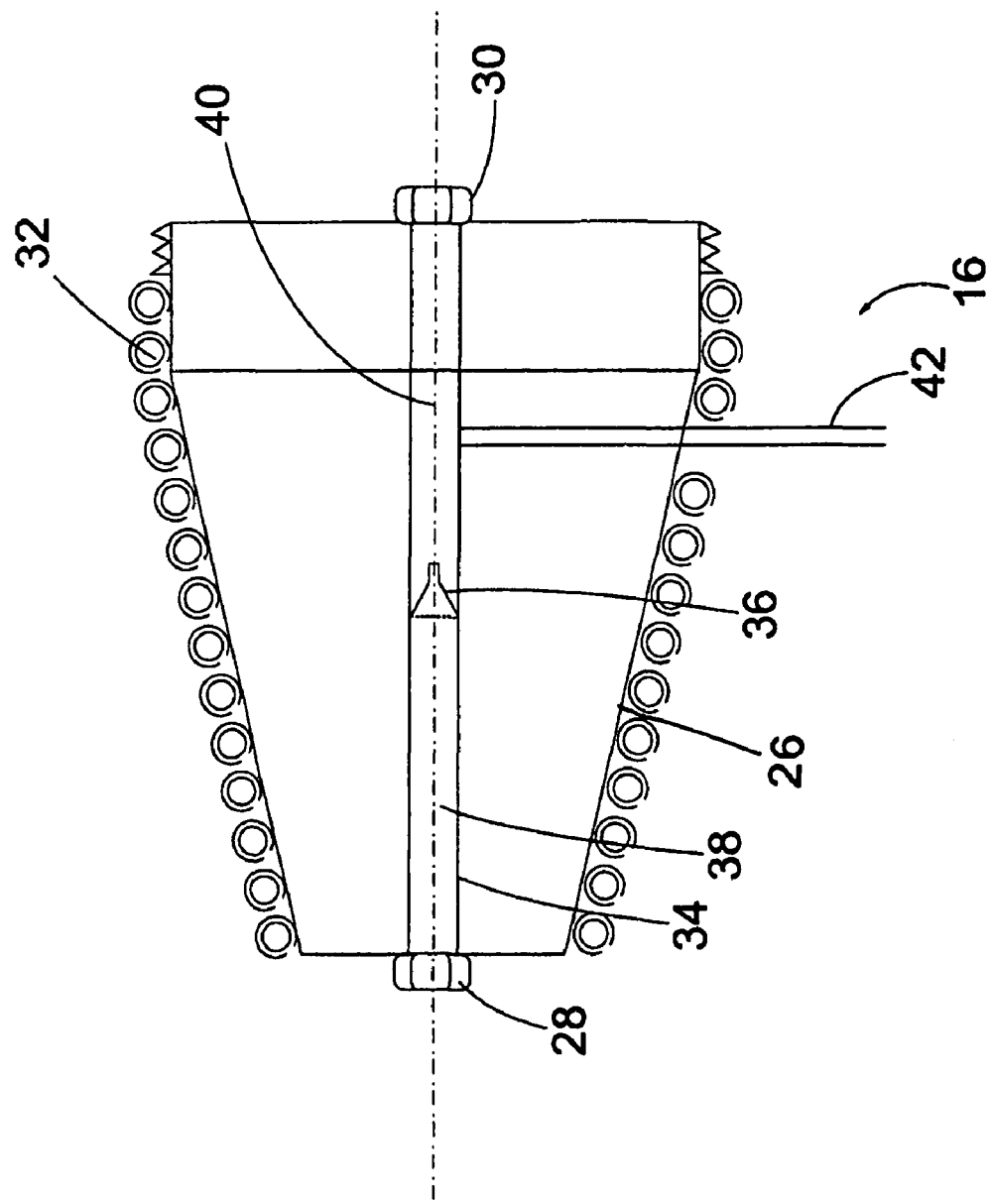
FIG. 2 shows the interface of FIG. 1 in detail.

After passing the column, the sample in the mobile solvent, which is still liquid, hot and under high pressure, reaches the interface 16. The interface 16 is again shown in detail in FIG. 2. It comprises a stainless steel cone 26 with connections 28 and 30. The HPLC column is screwed to the connection 28. The connection 30 forms the link to the sample volume of the detector 14. The cone 26 is completely surrounded by a heating wire 32. The heating wire 32 is connected to a control (not shown) to heat the cone in a range between room temperature and 400° C. Inside the cone 26 a tube 34 of stainless steel or ceramic is situated. The tube 34 connects the connection 28 with the connection 30. Behind the connection 28, approximately in the middle of the interface 16, a variable restrictor 36, particularly a frit, a critical nozzle, or an aperture plate, is disposed. The restrictor forms a throttle. In the zone 38 before the restrictor 36, the mobile solvent with the sample is liquid and under high pressure. Ambient pressure is present in the zone 40 behind the restrictor. Mobile solvent entering the zone 40 through the restrictor 36 is immediately evaporated. Thereby it cools down to a large extent.

The temperature, however, is maintained by the heater 32. No aerosol is formed. The now gaseous mobile solvent enters the sample volume of the detector 14 through the connection 30.

Behind the restrictor 36 the tube 34 has a connection 42 for dopant gas. Depending on the application, it can make sense to add additional dopant gas in the form of molecular hydrogen or oxygen. This facilitates the detection of less-volatile substances or substances difficult to excite in the sample volume.

Figure 3:
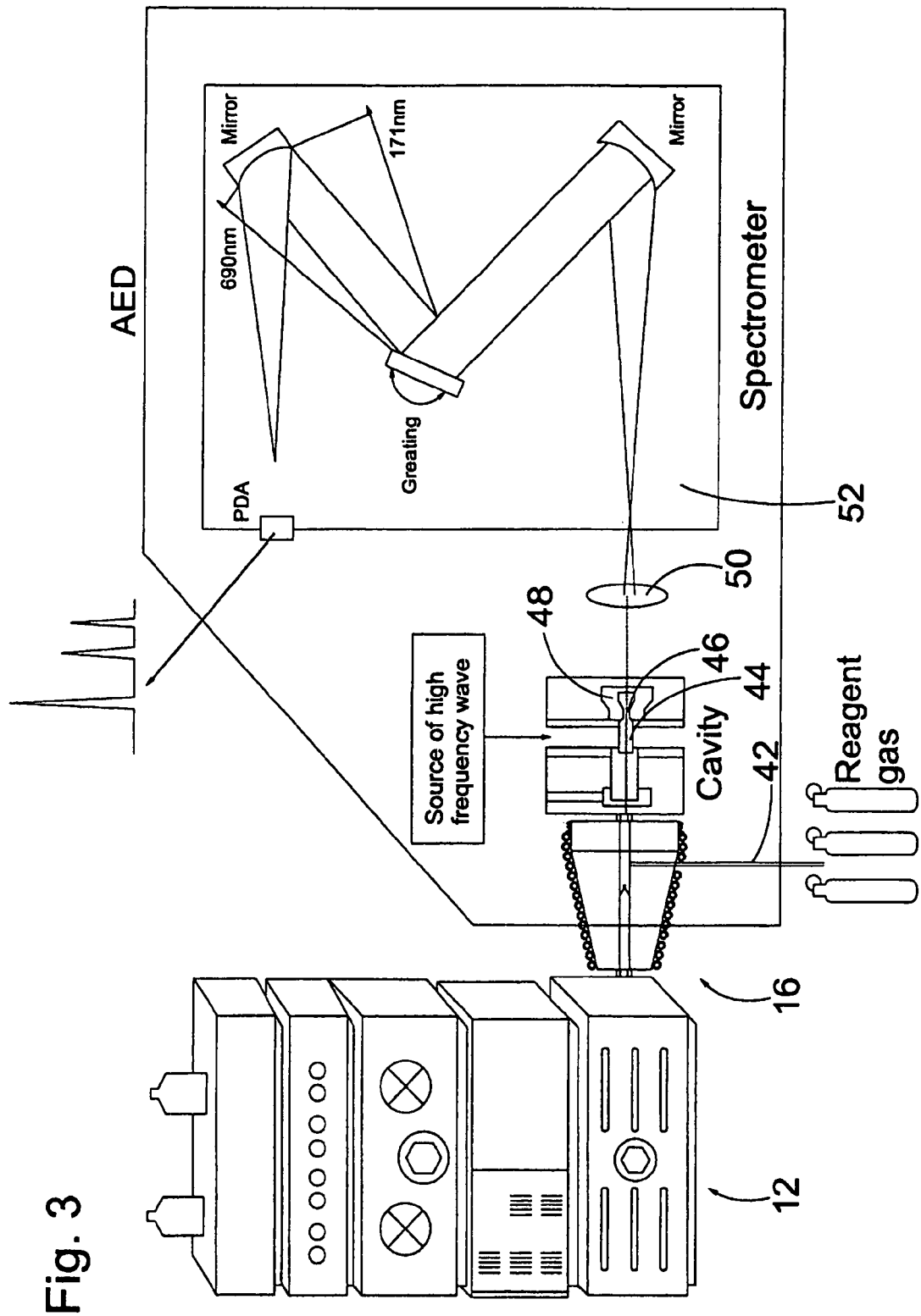
FIG. 3 shows the assembly of FIG. 1 with an atomic emission detector in detail.

In FIG. 3 the detector is shown in greater detail. The gas leaving the interface 16 at the connection 30 is immediately forwarded into the sample volume 44. The sample volume 44 is surrounded by a tube 46 which is located in a microwave generator 48. Helium is inserted into the tube 46, the microwave generator 48 inducing a helium plasma with a temperature of 2000 to 3000 K therein. The sample introduced into the plasma and the respective time-resolved components of the sample entering the plasma are now atomized and excited to emit element specific light.

The atoms and molecule fragments emit narrowband radiation on well-known wavelengths. This light is focused on the entrance slit of a spectrometer 52 with a lens 50. In the spectrometer 52 the light is dispersed by means of a grating and wavelength selectively detected by a photodetector. Depending on the position of the grating, another wavelength range can be imaged on the detector by rotation of the grating. In this way it is determined which element or which molecule fragment shall be detected.

The composition of the mobile solvent varies depending on the application problem. Water is used exclusively as mobile solvent for the determination of steroids. A mixture of water:acetonitrile:HCOOH in the ratio of 80:20:1 is used for the determination of antibiotics. However, in either case the portion of organic solvent is small. Thus, interferences by signals of organic components in the plasma are avoided or significantly reduced. Thereby the accuracy of the results as well as the dynamic range of the measurement are improved.

In an alternative embodiment an ICP-MS assembly is used as a detector instead of a microwave plasma. In this case the gas generated in the interface is directly forwarded into an argon plasma. The detection with the mass spectrometer is carried out in the common manner and does not have to be described here in more detailed. Interferences by undesirable organic background are significantly reduced as well. An assembly for removing the solvent before entering into the sample volume is not necessary.

In another embodiment the expansion and the phase change are separated from each other. For this purpose a cooling means is provided behind the restrictor. The mobile solvent is first of all expanded without phase change. Thereby an intermediate aerosol is formed which is introduced after the phase change into the sample volume. During this transition phase an opportunity to align, to accelerate and to select the particles or molecules is provided before the mobile solvent is transferred into the gaseous state.

In another embodiment the mobile solvent is expanded immediately into the plasma inside the sample volume. For this purpose the restrictor is made of high temperature resistant ceramic and is arranged inside the plasma.

The invention claimed is:

1. Assembly for determining material properties and/or material concentrations of components of a sample, comprising:
   (a) a chromatographic separating column adapted to operate with a liquid mobile solvent, said chromatographic separating column having an inside, said inside of said chromatographic separating column having a temperature, and an outside, said outside having ambient temperature and ambient pressure;
   (b) means for controlling said temperature between room temperature and 250° C;
   (c) means for creating an increased pressure level which is greater than ambient pressure within said inside of said chromatographic separating column; and
   (d) a detector having a sample volume, said sample volume adapted to insert said components of said sample, and wherein
   (e) an interface is provided between said separating column and said detector, said interface comprising:
      an interface body,
      an inlet for the liquid mobile solvent from the separating column,
      an outlet to the sample volume of the detector,
      a tube extending through the interface body connecting the inlet and the outlet; and
      a restrictor inside said tube positioned between the inlet and the outlet, wherein said restrictor is adapted to expand said mobile solvent from said increased pressure level inside said separating column to said ambient pressure producing a phase change of said mobile solvent from liquid to gaseous phase without forming an aerosol, wherein said mobile solvent containing said sample is liquid upstream of said restrictor and is exposed to an increased pressure, and wherein said ambient pressure is present downstream of the restrictor;
   (f) means are provided for heating a zone in the tube within the interface body downstream of the restrictor; and
   (g) means are provided for transferring said gaseous mobile solvent containing said components of said sample from the outlet into said sample volume of said detector.

2. Assembly according to claim 1, wherein said chromatographic separating column is a High Temperature HPLC column.

3. Assembly according to claim 1, wherein said component of said sample in said sample volume is excited to emit light, said light being composed of a plurality of wavelengths, and wherein said light emitted by said component of said sample is selectively detectable with respect to said wavelengths.

4. Assembly according to claim 1, wherein a mass spectrometer is provided for mass spectrometric analysis of said components of said sample in said sample volume.

5. Assembly according to claim 1, wherein a microwave plasma is provided in said sample volume.

6. Assembly according to claim 1, wherein an inductively coupled plasma is provided in said sample volume.

7. Assembly according to claim 1, wherein said heating means have a heating power, said heating power being sufficient to mainly atomize said components of said sample.

8. Assembly according to claim 1, comprising means to feed one or more dopant gases into said sample volume.

9. Assembly according to claim 1, comprising a mixture of a water portion and acetonitrile as mobile solvent and wherein said water portion amounts to at least 50 vol %.

10. Assembly according to claim 1, wherein a mixture of water, acetonitrile and HCOOH is provided as mobile solvent in a selected volumetric ratio and that said volumetric ratio of said components water:acetonitrile:HCOOH is about 80:20:1.

11. Method for determining material properties and/or material concentrations of components of a sample comprising said steps of:
   (a) introducing a sample into a chromatographic separating column under elevated pressure with a mobile solvent in liquid phase mainly containing water;
   (b) heating said separating column to a temperature inside said separating column sufficient to separate said components of said sample from each other while passing through said separating column, said mobile solvent being in liquid phase and at an elevated pressure level;

(c) introducing said mobile solvent containing said components from said heated separating column into an interface tube in an interface body and having a restrictor inside said interface tube within said interface body along with a means for heating a zone of the interface tube within the interface body downstream of the restrictor within the tube to thereby expand said liquid phase mobile solvent with said separated components through the restrictor in the tube from the elevated pressure level inside said separating column to ambient pressure downstream of said restrictor thereby producing a phase change of said mobile solvent from a liquid to a gaseous phase without forming an aerosol;

(d) transferring said gaseous mobile solvent containing said components of said sample into a sample volume of a detector; and (e) detecting said components of said sample.

12. Use of a liquid containing mainly or exclusively water as mobile solvent in an assembly according to claim 1, comprising the steps of:

(a) obtaining an assembly for determining material properties and/or material concentrations of components of a sample as defined by claim 1 and having an inlet for inputting a sample in a mobile solvent into the assembly;

(b) obtaining a sample for which material properties and/or material concentrations of components are to be determined;

(c) mixing the sample with a liquid containing mainly or exclusively water;

(d) inputting the mixture of sample and liquid into the input;

(e) operating the assembly; and (f) determining from the detector of the assembly of claim 1 material properties and/or material concentrations of components of the sample.

13. Interface for connecting a detector to a chromatographic separating column, comprising:

connecting means for connecting a chromatographic separating column at an increased temperature and having an increased pressure relative to ambient pressure for liquid mobile solvents of mainly water;

a tube and a restrictor inside said tube, wherein said restrictor is adapted to expand said mobile solvent from an increased pressure level inside said separating column to said ambient pressure and producing a phase change of said mobile solvent from liquid to gaseous phase without forming an aerosol and wherein said mobile solvent containing said sample is liquid upstream of said restrictor and is exposed to an increased pressure and wherein said ambient pressure is present downstream of said restrictor;

means for heating at least a zone of said tube downstream of said restrictor;

means for transferring said gaseous mobile solvent containing said components of said sample into a sample volume of said detector;

an interface body having an inlet end mounting the connecting means for connecting a chromatographic separating column and an outlet end mounting the means for transferring said gaseous mobile solvent containing said components of said sample into the sample volume of said detector, wherein the tube extends through the interface body connecting the connecting means mounted on the inlet end and the transferring means mounted on the outlet end with the restrictor inside the tube positioned between the inlet end and the outlet end, and wherein the means for heating at least a zone of the tube downstream of the restrictor heats the tube within the interface body.

14. Interface according to claim 13, wherein the interface body is hollow and the tube extends through the hollow body.

15. Interface according to claim 14, wherein the means for heating a zone in the tube downstream of the restrictor is heating wire surrounding the body.

16. Interface according to claim 15, wherein the interface body is substantially in the shape of a truncated cone with the inlet at the apex end of the cone and the outlet at the base of the cone, and wherein the means for heating a zone in the tube downstream of the restrictor is heating wire surrounding the body between the apex end and the base end.

17. Assembly according to claim 1, wherein the interface body is hollow and the tube extends through the hollow body.

18. Assembly according to claim 17, wherein the means for heating a zone in the tube downstream of the restrictor is heating wire surrounding the body.

19. Assembly according to claim 18, wherein the interface body is substantially in the shape of a truncated cone with the inlet at the apex end of the cone and the outlet at the base of the cone, and wherein the means for heating a zone in the tube downstream of the restrictor is heating wire surrounding the body between the apex end and the base end.

* * * * *